(12) United States Patent
Gastaldo et al.

(10) Patent No.: US 9,007,456 B2
(45) Date of Patent: Apr. 14, 2015

(54) DEVICE AND METHOD FOR INSPECTING SEMICONDUCTOR WAFERS

(75) Inventors: Philippe Gastaldo, Pontcharra (FR); François Berger, Four (FR); Cleonisse Serrecchia, Chapareillan (FR)

(73) Assignee: Altatech Semiconductor, Montbonnot-Saint-Martin (FR)

( * ) Notice: Subject to any disclaimer, the term of this patent is extended or adjusted under 35 U.S.C. 154(b) by 1106 days.

(21) Appl. No.: 12/992,236

(22) PCT Filed: May 11, 2009

(86) PCT No.: PCT/FR2009/000544
§ 371 (c)(1),
(2), (4) Date: Feb. 10, 2011

(87) PCT Pub. No.: WO2009/141534
PCT Pub. Date: Nov. 26, 2009

(65) Prior Publication Data
US 2011/0128371 A1    Jun. 2, 2011

(30) Foreign Application Priority Data

May 13, 2008 (FR) ...................................... 08 02586

(51) Int. Cl.
| | |
|---|---|
| *H04N 7/18* | (2006.01) |
| *H01L 21/67* | (2006.01) |
| *G01N 21/95* | (2006.01) |
| *H01L 21/687* | (2006.01) |

(52) U.S. Cl.
CPC ...... *H01L 21/67288* (2013.01); *G01N 21/9501* (2013.01); *H01L 21/68707* (2013.01)

(58) Field of Classification Search
CPC . G01R 31/209; G01N 21/9501; G01N 25/956
USPC ...................................................... 348/87, 126
See application file for complete search history.

(56) References Cited

U.S. PATENT DOCUMENTS

| | | | | |
|---|---|---|---|---|
| 5,008,542 | A | * | 4/1991 | Look et al. .................. 250/341.4 |
| 5,233,203 | A | * | 8/1993 | Haga ........................ 250/559.41 |
| 5,923,020 | A | | 7/1999 | Shuji et al. |

(Continued)

FOREIGN PATENT DOCUMENTS

| | | |
|---|---|---|
| EP | 1194803 | 4/2002 |
| JP | 08125004 | 5/1996 |

(Continued)

OTHER PUBLICATIONS

Search Report for PCT Application No. PCT/FR2009/000544.

*Primary Examiner* — Jeremaiah C Hallenbeck-Huber
(74) *Attorney, Agent, or Firm* — Meyertons, Hood, Kivlin, Kowert & Goetzel, P.C.; Eric B. Meyertons (57) ABSTRACT

Semiconductor wafer inspection device comprising a wager transport arm provided with at least one wafer support element, a wafer gripper, the gripper having two distant branches designed to take hold of the opposed edges of the wafer, the gripper being mounted so as to rotate on a shaft in order to be able to rotate the wafer between an approximately horizontal position and an approximately vertical position, and at least two inspection systems placed on one side of the wafer and on the other, in an approximately vertical position symmetrically with respect to the plane passing through the wafer.

17 Claims, 5 Drawing Sheets

(56) References Cited

U.S. PATENT DOCUMENTS

| | | | |
|---|---|---|---|
| 5,933,230 A * | 8/1999 | Imaino et al. | 356/237.2 |
| 6,271,925 B1 * | 8/2001 | Muller | 356/512 |
| 6,628,381 B1 * | 9/2003 | Komem et al. | 356/237.4 |
| 6,648,730 B1 | 11/2003 | Chokshi et al. | |
| 6,693,708 B1 | 2/2004 | Hunter | |
| 6,748,293 B1 | 6/2004 | Larsen | |
| 7,304,731 B2 * | 12/2007 | Hill | 356/237.2 |
| 2004/0012775 A1 | 1/2004 | Kinney et al. | |
| 2004/0032581 A1 * | 2/2004 | Nikoonahad et al. | 356/237.2 |
| 2004/0174518 A1 * | 9/2004 | Naiki et al. | 356/237.2 |
| 2004/0239920 A1 * | 12/2004 | Kreh et al. | 356/237.3 |
| 2005/0146719 A1 * | 7/2005 | Chhibber et al. | 356/370 |
| 2005/0219521 A1 * | 10/2005 | Vollrath et al. | 356/237.2 |
| 2005/0232735 A1 * | 10/2005 | Yazawa | 414/416.03 |
| 2005/0237520 A1 * | 10/2005 | Tillmann | 356/244 |
| 2006/0018748 A1 | 1/2006 | Tran | |
| 2006/0182334 A1 | 8/2006 | Akimoto | |
| 2006/0213537 A1 * | 9/2006 | Atalla | 134/18 |
| 2006/0244955 A1 | 11/2006 | Schramm et al. | |
| 2007/0103676 A1 | 5/2007 | Marxer et al. | |
| 2007/0188745 A1 | 8/2007 | Smedt | |
| 2008/0007726 A1 | 1/2008 | Fairley et al. | |
| 2009/0136117 A1 * | 5/2009 | Barkol et al. | 382/145 |

FOREIGN PATENT DOCUMENTS

| | | |
|---|---|---|
| JP | 08327554 | 12/1996 |
| JP | 08335614 | 12/1996 |
| JP | 10056046 | 2/1998 |
| JP | 11121577 | 4/1999 |
| JP | 11219990 | 8/1999 |

* cited by examiner

Single arm turret          Fig. 7

Fig.9

DEVICE AND METHOD FOR INSPECTING SEMICONDUCTOR WAFERS

BACKGROUND OF THE INVENTION

1. Field of the Invention

The invention relates to the field of inspection and verification of semiconductor wafers or substrates during or at the end of production, or during the production of integrated circuits.

2. Description of the Relevant Art

As a result of the tendency to increase the diameters of semiconductor wafers, they must be handled with extreme care and are increasingly fragile. Furthermore, the increasingly fine engraving of the patterns of a semiconductor wafer makes each component of the wafer more and more susceptible to production faults.

In conventional manner, semiconductor wafers are visually inspected by an operator. The human eye is capable of detecting relatively small faults on semiconductor wafers which have, to the untrained eye, the appearance of a mirror. The greater the production quality, the better the human eye is capable of locating small faults. However, the fact that engraving techniques are becoming increasingly fine means that the human eye is reaching its limits, in particular for specific types of fault.

Furthermore, the task of visually inspecting semiconductor wafers is slow and fastidious. In a clean room for producing semiconductor wafers, it is desirable to reduce the presence of humans. Visual inspection is also found to be costly. The inspection machines are generally slow and bulky, which is a significant disadvantage in a clean room whilst using electromagnetic radiation which requires specific protection for the operators. Finally, the visual inspection does not generate adequate statistical data relating to the positions, sizes or types of fault, which is indispensable for the statistical monitoring of methods and research into the causes of faults or problems.

SUMMARY OF THE INVENTION

The invention is intended to improve the situation.

The semiconductor wafer inspection device comprises a wafer transport arm which is provided with at least one wafer support element, a gripper for gripping wafers, at least one light source and at least one camera arranged at one side and at least two inspection systems which are arranged at one side and the other of the wafer in its substantially vertical position, symmetrically relative to the plane which extends through the wafer. Each camera of an inspection system can be positioned to capture the light reflected by the surface of the wafer opposite it. Each light source can be positioned to transmit an incident beam towards the surface. The gripper may comprise two remote limbs which are configured to hold opposite edges of the wafer. The gripper can be rotatably mounted on a shaft in order to be able to rotate the wafer between a substantially horizontal position and a substantially vertical position.

The method for inspecting semiconductor wafers comprises the following steps:
- a semiconductor wafer to be inspected is conveyed by at least one support element belonging to a transport arm,
- the remote limbs which form part of a gripper grip opposite edges of the wafer,
- the gripper rotates about a shaft which causes the wafer to move from a substantially horizontal position to a substantially vertical position, and
- at least two inspection systems which are arranged at one side and the other of the wafer in its substantially vertical position, symmetrically relative to the plane which extends through the wafer, are actuated.

BRIEF DESCRIPTION OF THE DRAWINGS

The invention will be better understood from a reading of the detailed description of embodiments set out by way of non-limiting example and illustrated with reference to the appended drawings, in which.

DETAILED DESCRIPTION OF THE PREFERRED EMBODIMENTS

Generally, current inspection machines are provided for a semiconductor wafer in a horizontal position resting on a plate, see US 2008/0007726, JP 100 56 046 and KR 2004 0024795. The same applies to document EP 1 194 803 which further proposes a complex catadioptric structure.

The Applicant has realised that the inspection of semiconductor wafers in a horizontal position had various disadvantages. On the one hand, the surface flatness of the wafers is affected by gravity and therefore a deformation under the effect of its own weight, this being more significant as the diameter of the wafer increases. The wafers may have a diameter of 300 mm, even 450 mm. The solution generally selected involves using a reference surface having a surface flatness greater than that which can be measured, on which the wafer is positioned or held during the measuring operation. This reference surface is generally that of a solid support. The contact between this surface and the wafer is a source of contamination of the rear face. On the other hand, this method masks the rear face during the measuring of the front face.

Document US 2006/0018748 describes a photomask inversion mechanism which allows one face and then the other of a photomask to be inspected by an inspection machine. The inversion mechanism is unsuitable for industrial volumes in that it tends to divide by two the yield of the actual inspection machine. Furthermore, the photomask is carried only by its edges in the horizontal position during the inspection, which indicates that the photomask has a high thickness to length ratio, which is not the case for semiconductor wafers.

Document US 2007/0188745 describes a device for inspecting the two faces of a semiconductor wafer in an oblique position. A semiconductor wafer is arranged on an air support mechanism which allows the semiconductor wafer to be supported in a floating manner. The lower face of the semiconductor wafer is inspected by a scanning head which can be moved in translation along an axis, the scanning head having a length which is much smaller than the diameter of the semiconductor wafer. The semiconductor wafer is rotatably driven by support rollers against which the edge of the semiconductor wafer abuts. By combining the rotation of the wafer and the translation movement of the scanning head, the lower surface of the wafer can be progressively inspected, the inclined position providing a degree of support for the edge of the wafer on the rollers. However, the inspection of the upper face requires special means owing to the inclination of the wafer. The inspection of the lower face is particularly slow owing to the actual structure of the device. The wafer is at risk of vibrating and/or becoming deformed under the flow of air which holds it in a floating position.

Owing to the invention, the wafer which is held so as to be fixed in a substantially vertical position during the inspection has a particularly reduced risk of deformation. The term substantially vertical is understood to be to within +/−5°. The symmetrical structure of the device allows a regular laminar air flow within the device and reduces the risk of the semiconductor wafer becoming contaminated with dust or other harmful elements during the inspection (this cannot be the case during an inspection in the inclined position, since the air is unilaterally deflected).

Furthermore, the impact of the flow of air on the mechanical stability of the semiconductor wafer is reduced. The mechanical vibrations are reduced. The vertical position at the semiconductor wafer prevents a deformation under its own weight, which avoids use of a costly and heavy rectified plate. The risk of contamination of the lower surface of the semiconductor wafer is particularly reduced, in so far as the wafer is gripped by grippers which come into contact with the outer edge thereof.

The lower surface of the semiconductor wafer is available for an inspection which can take place in the same vertical position which increases the possibility of establishing correlations between the faults of the upper surface and the faults of the lower surface. Furthermore, the fact that the inspection of the rear surface is carried out in the same position as the inspection of the upper surface allows a significant time saving. The stability of the semiconductor wafer during the measurement operations reduces the risks of contamination, drastically reduces mechanical vibrations and increases the reliability of the measurements.

The opposite surfaces of the wafer are conventionally referred to as the upper surface and lower surface, even when the wafer is in a vertical position with reference to the horizontal position of the wafer supported by the fork, before and after the inspection in the vertical position.

The support elements provided to support a wafer upstream and downstream of the gripper may form a fork. The support elements may thus move the wafer into a horizontal position whilst remaining remote from the limbs of the gripper. The fork provides good mechanical stability of the semiconductor wafer and deformation under its own weight within acceptable limits during transport. The transport arms may comprise at least two articulation axes. The transport arm may be supported by a turret. The turret can support two wafer transport arms. The turret can be mounted for translation on a sliding member. The turret with two transport arms allows the movement of the wafer to be optimised between a store for wafers and the gripping gripper.

Each limb of the gripper may have a groove which is provided on a surface which is arranged opposite the other limb. The groove can be configured in accordance with the shape of the edge of the wafer. The groove may be generally V-shaped in axial section. The groove can ensure self-centering of the wafer.

At least one of the limbs of the gripper is pivotably mounted along an axis which is substantially perpendicular relative to the plane of the wafer held between the limbs. Preferably, the two limbs are pivotably mounted along parallel axes or along a common axis. The transport elements may have a lateral spatial requirement less than the opening between the limbs of the gripper. The risks of mechanical interference between the transport elements and the gripper are thus limited.

Each source of light may comprise a monitor having a diagonal which is greater than the maximum opening between the limbs of the gripper. Excellent illumination of the opposing surfaces of the semiconductor wafer is thus ensured. The light source may comprise an LCD or plasma screen. The camera can be arranged above the corresponding source of light.

The device may comprise a control unit which is configured to control the display of parallel lines by the light sources. The control unit can be configured to control an alternating arrangement of vertical and horizontal lines displayed by the light sources.

The control unit may comprise at least one output which is connected to a camera and at least one output which is connected to the corresponding light source in order to synchronise the camera and the light source. Advantageously, the control unit controls the two cameras and the two symmetrical sources of light with parameters such as the exposure times or the illumination mode specific to the characteristics of each face.

The control unit can be configured to control an illuminated oval zone of the light source and a dark outer edge. The light reaching the surface of the semiconductor wafer is thus optimised, increasing the proportion of incident light. In the same manner, the proportion of incident or diffused light captured by the cameras is reduced. The saturation decreases. The contrast is thereby improved.

The control unit can be configured to control the display of different colours simultaneously by the sources of light in order to optimise the detection quality.

The control unit may be configured to control an illumination which is alternated by the light sources. The proportion of diffused light reaching the cameras is thus reduced. When the semiconductor wafer is illuminated by a light source, a portion of the incident beam can pass through the semiconductor wafer and be subject to phenomena of diffraction and reach the camera located at the opposite side. Of course, this phenomenon is dependent on the reflectivity of the semiconductor wafer. In the case of a particularly reflective wafer, the phenomenon is relatively harmless and the illumination may be simultaneous. In contrast, in the case of a relatively non-reflective semiconductor wafer, the alternating illumination allows better resolution of the detection.

The control unit can be configured to control the taking of images by the cameras in an alternating or simultaneous manner, in particular in synchronisation with alternating or simultaneous illumination. Each image can be taken for an exposure time of approximately from 100 to 3000 milliseconds. The transfer time by the cameras can be in the order of from 5 to 600 milliseconds. The simultaneous or alternating taking of images allows the duration of the inspection to be optimised compared with an inspection of one face and then the other.

Furthermore, the cameras may be provided with an electronic or mechanical shutter. The synchronisation between the taking of images with a camera and the illumination by the corresponding light source may replace the electronic or mechanical shutter whilst ensuring that quality images are taken. In this instance, the duration of the illumination may be between 100 and 3000 milliseconds.

The cameras may be provided with an objective lens, referred to as a pivoting lens. It is possible better to observe the edges of the semiconductor wafer owing to the pivoting of the focal plane.

The LCD or plasma screen of the monitor may comprise a frosted panel which allows a reduction in fringe residues which are linked to the generation of a harmonic which is connected to the periodicity of the pixels of the screen and the presence of dead zones. The frosting may be carried out using acid or by mechanical frosting of the sanding or polishing type. In this manner, a fault inspection precision is obtained in the order of a nanometer perpendicularly relative to the surface observed.

Figure 1:
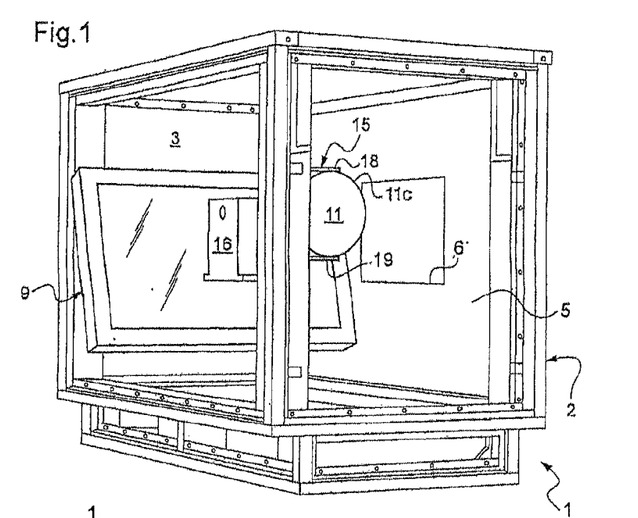
FIG. 1 is a schematic perspective view of a machine for inspecting flat discs, such as semiconductor wafers, an inspection system having been omitted for better understanding of the drawing.
Figure 2:
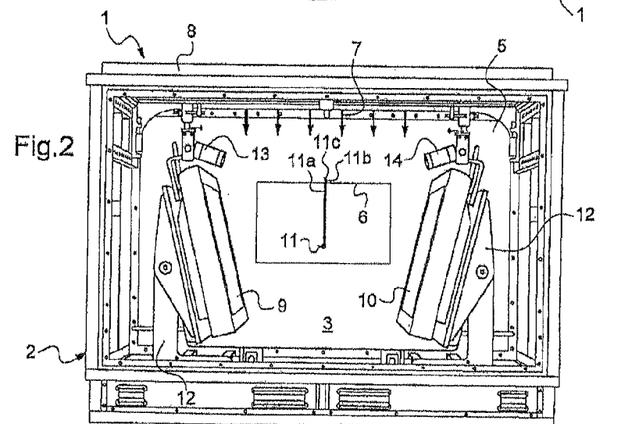
FIG. 2 is a front elevation of the machine of FIG. 1, the cover and chassis elements having been omitted for better understanding of the drawing.
Figure 3:
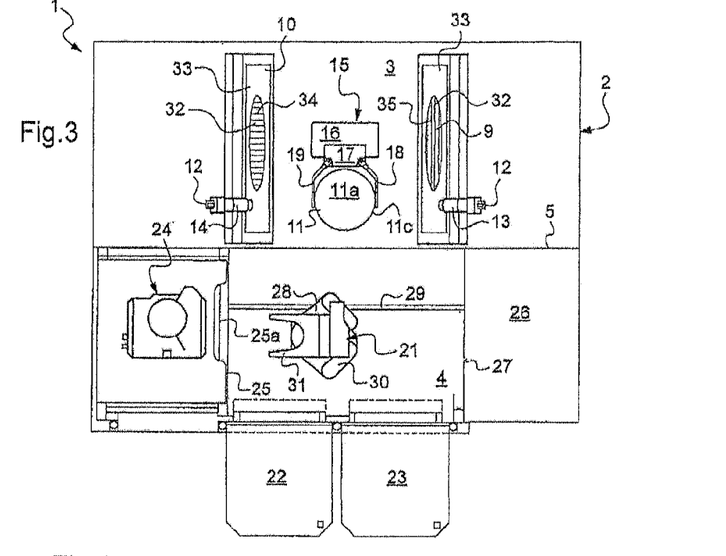
FIG. 3 is a plan view of the machine of FIG. 1.

In FIGS. 1 to 3, the inspection machine 1 has been illustrated with the cover open. More precisely, in FIG. 1, the front cover and one of the lateral covers are open. In FIG. 2, the front cover is open. In FIG. 3, the top cover is open. Of course, in the operating state, the inspection machine 1 is provided with covers thereof closed. The covers are opaque in order to prevent the introduction of parasitic light which is capable of interfering with the cameras. Furthermore, in FIG. 1, one of the two screens, the corresponding camera and the support of the gripper have been omitted so that the other components can be better seen. In the same manner, in FIG. 2, the gripper and the gripper support have been omitted, the substrate being presented there in the inspection position which is substantially vertical.

As can be seen in FIGS. 1 to 5, the inspection machine 1 comprises a frame 2, for example, of the mechanically welded type, which forms an inspection chamber 3 and a supply chamber 4 which are separated by a partition 5 through which an aperture 6 extends. The frame 2 is covered by the covers.

The inspection chamber 3 has a symmetrical structure relative to a vertical plane which extends through the centre of FIGS. 2 and 3. The inspection machine 1 comprises a supply 8 of filtered air of the laminar type which allows a movement of air to be generated in the direction from the top to the bottom of the chamber 3 as illustrated by the arrows 7. The supply 8 of air also forms the upper wall of the chamber 3. The floor of the measuring chamber is constituted by a stack of 2 grids, one of which can be offset from the other, which allows the flow of air leaving this output to be controlled and thereby allows the excess pressure in the measuring chamber to be controlled.

The inspection machine 1 comprises two video screens 9 and 10 which are mounted symmetrically, in particular relative to a vertical plane which extends through the centre of the inspection machine 1 or which extends through the substrate 11 to be inspected which is held in a vertical position, see FIGS. 1 and 2. Each screen 9, 10 rests on a support 12, for example, of the articulated type which allows orientation of the screen 9, 10 along an axis which is substantially parallel relative to the plane of the substrate 11, for example, a substantially horizontal axis, and adjustment in translation of the position of the screen 9, 10 relative to the measured surface. The screens 9 and 10 are mounted opposite each other remotely and are orientated slightly in an upward direction, for example, with an angle of between 10 and 30°. The screens 9 and 10 may be of the LCD or plasma type. The screens 9, 10 have a height which is greater than 1.6 times the diameter of the substrate to be inspected, for example, a height of 54 cm for a substrate with a diameter of 300 mm and a height of 72 cm for a substrate with a diameter of 450 mm.

The sides of the illumination screen are conventionally referred to as the height and width. The height is intended to be understood to be the smallest dimension of the display zone of the screen, with reference to the orientation of the screen when the screen is used as a conventional video display device.

The inspection machine also comprises two cameras 13, 14 which are located in the inspection chamber 3. The cameras 13, 14 can be supported by the supports 12. A support 12 is common to a screen 9 or 10 and a camera 13 or 14. The camera 13 is hidden in FIG. 1 by a pillar of the frame 2. The cameras 13, 14 can also be adjusted in terms of position, in particular in terms of height, width and length, the length corresponding to the horizontal distance relative to the substrate 11. Furthermore, the cameras 13 and 14 can be adjusted in terms of angular orientation. The cameras may be of the CCD type (Charge Coupled Device) or CMOS type (Complementary Metal Oxide Semiconductor). The screen 9 and the camera 13 form a first inspection system. The screen 10 and the camera 14 form a second inspection system. The first and second inspection systems are symmetrical. The respective positions of the screen 9, the substrate 11 and the camera 13 at one side, the screen 10, the substrate 11 and the camera 14 at the other side of the inspection chamber 3 are selected so that each screen 9, 10 transmits an incident beam which reaches the substrate 11 at its corresponding face 11a, 11b, respectively, and the camera 13, 14 captures the beam reflected by the surface 11a, 11b. The faces 11a and 11b are parallel. The incident beam does not completely reach the substrate 11. The relative positions are selected so that the surface 11a, 11b is sufficiently illuminated to allow the camera 13, 14 to detect a light signal which is representative of faults in the surface 11a, 11b. The luminosity and contrast of the screen 9, 10 are adjusted to high levels to promote the detection of faults by the cameras 13, 14. Furthermore, the inactive surfaces of the chamber 3 have maximum absorption of the wavelengths used. That is to say, the inactive surfaces of the inspection chamber 3 are black. The interference of the cameras 13, 14 is thereby limited.

Since the cameras 13, 14 are inclined relative to the normal to the surfaces 11a, 11b, they have a slight distortion, the distance between the upper end of the surface 11a and the objective lens of the camera being less than the distance between the lower end of the surface 11a and the objective lens of the camera 13. The same applies to the camera 14 relative to the surface 11b facing it. To this end, the cameras 13, 14 may comprise a pivoting objective lens which allows the distortion to be reduced and better observation to be achieved for the peripheral zone of the surfaces 11a and 11b.

The inspection machine 1 comprises a gripper 15 for retaining the substrate 11. The gripper 15 which can be seen in FIGS. 1 and 3 is illustrated in greater detail in FIGS. 4 and 5 which provide the substrate 11 with a horizontal receiving position and vertical inspection position, respectively. The gripper 15 comprises a base 16 which rests on the frame 2, a turret 17 and two limbs 18 and 19. The base 16 may generally have a rectangular parallelepipedal shape. The turret 17 is articulated to the base 16 along a substantially horizontal axis which extends via the aperture 6. The turret is capable of ensuring a rotation of at least 90°. A rotation of 180° may allow a substrate 11 to be inverted which may be found to be advantageous in some applications. The rotation of the turret 17 may be provided by an electromechanical driving device which is arranged in the base 16, for example, a step motor.

The limbs 18 and 19 are symmetrical relative to a plane normal with respect to the substrate 11 when the substrate 11 is carried by the limbs 18 and 19. Each limb 18, 19 is articulated to the turret 17 along its own axis, which is offset relative to the pivot axis of the turret 17 and normal with respect to the substrate 11. In a variant, the limbs 18 and 19 may be coaxial.

Figures 4, 6:
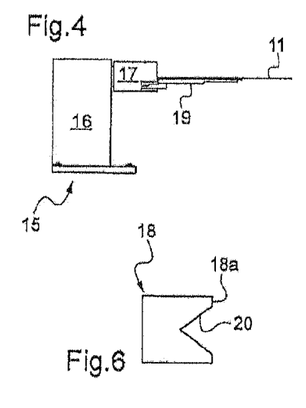
FIG. 4 is a schematic side view of the gripper in a first position.
FIG. 6 is a cross-section view of a limb of the gripper.
Figure 5:
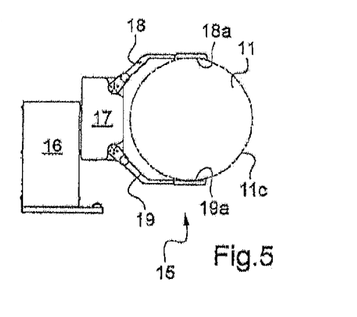
FIG. 5 is a schematic side view of the gripper in a second position.

In another variant, one of the limbs is stationary relative to the turret 17 and the other limb is articulated. The turret 17 comprises a member for actuating the limbs 18, 19, for example, in the form of two step motors or one step motor and a gear mechanism which allows the limbs 18 and 19 to remain symmetrical regardless of their angular position. The limbs 18 and 19 can pivot between two operating positions, an open position used to move the substrate 11 closer or further away and a position in engagement with the outer edge 11c of the substrate 11. FIGS. 4 and 5 illustrate the position in engagement.

More specifically, each limb 18, 19 has a bent shape so that the spatial requirement of the turret 17 is less than the diameter of the substrate 11. That is to say, the limbs 18, 19 are in the form of a circumflex accent. The limbs 18, 19 each have an inner face 18a, 19a which is opposite the inner face of the other limb 19, 18 and which is provided to come into contact with the outer edge 11c of the substrate 11. The inner face 18a, 19a has an elongate groove 20 parallel with the pivot axis of the turret 17. The groove 20 which can be seen in FIG. 6 may have a cross-section which is V-shaped, or alternatively in the form of a semi-circle or ogive, to co-operate in an appropriate manner with the outer edge 11c of the substrate 11 and to provide retention both in the horizontal position of the substrate 11 illustrated in FIG. 4 and in the vertical position illustrated in FIG. 5 and in intermediate positions with a slight clamping action which reduces to negligible values the deformation of the substrate 11, in particular the buckling in the inspection position.

The inspection machine 1 comprises a substrate handling member 21 which is provided to bring a substrate 11 to the gripper 15 before inspection and to unload the substrate from the gripper 15 after the inspection. The handling member 21 is arranged in the supply chamber 4. The handling member 21 may be in the form of a robot which is provided with an operating element which is capable of passing through the aperture 6 provided in the partition 5.

The inspection machine 1 comprises two containers 22, 23 which can be removed to store a plurality of substrates 11. The containers 22, 23 are supported by a wall of the chamber 4 at the side opposite the internal partition 5. The containers 22, 23 may be of the self-closing type so as to close during a separation with respect to the inspection machine 1. In the same manner, the wall of the handling chamber 4 is provided with an aperture in the region of the containers 22, 23, preferably provided with an automatic shutter which closes the supply chamber 4 before the containers 22, 23 are completely removed. The contamination of the substrates 11 and the chambers of the inspection machine 1 by dust is thereby limited.

The inspection machine 1 comprises a prealignment member 24 for the substrates 11. The prealignment member 24 may be arranged along the partition 5 at a longitudinal end of the supply chamber 4. The prealignment member 24 and the supply chamber 4 are separated by a partition 25 through which there extends an opening 25a which allows the passage of a substrate 11 which is carried by the handling member 21. Furthermore, the inspection machine 1 comprises a control and processing unit 26 which can be in the form of an electronic scanner. The control unit 26 is arranged at the end of the supply chamber 4 opposite the prealignment member 24 with a separation partition 27. The processing unit 26 can also be in contact with the partition 5. The control unit 26 is connected to the screens 9 and 10, to the cameras 13 and 14, to the gripper 15 and to the handling member 21.

The handling member 21 comprises a turret 28 which is capable of moving in translation relative to the frame 2 along an axis parallel with the partition 5. In this manner, the handling member 21 can move close to the opening 25a in the direction towards the prealignment member 24 in one position and move in the region of the aperture 6, opposite the gripper 15, in another position, or opposite the container 22 or opposite the container 23. The turret 28 can move along a sliding member 29 which is fixedly joined to the frame 2. The handling member 21 comprises an arm 30 having two articulation axes, supported by the turret 28, and a fork 31 supported by the end of the arm 30 opposite the turret 28. The articulation axes of the arm 30 may be substantially vertical. That is to say, the arm 30 is provided with two mutually parallel articulation axes normal with respect to the plane of a substrate 11 resting on the fork 31.

The fork 31 may be in the form of a plate having a substantially constant thickness and a generally rectangular contour with a large cut-out provided from one short side, allowing two teeth to remain. The cut-out may generally have a slightly flared U-shape. The teeth of the fork 31 form a substrate transport element. The spacing between the teeth of the fork 31 may be adapted to the diameter of the substrate to be handled, for example, of between 150 and 250 mm for a substrate having a diameter of 300 mm or between 225 and 400 mm for a substrate having a diameter of 450 mm. The fork 31 is provided with a movement in a horizontal plane owing to the movement of the turret 28 on the slide 29 and to two rotations allowed by the two articulation axes of the arm 30. The handling member 21 comprises a mechanism for vertical movement, in particular in translation in order to adjust the height of the fork 31 and consequently the substrate 11 carried by the fork 31.

Figure 7:
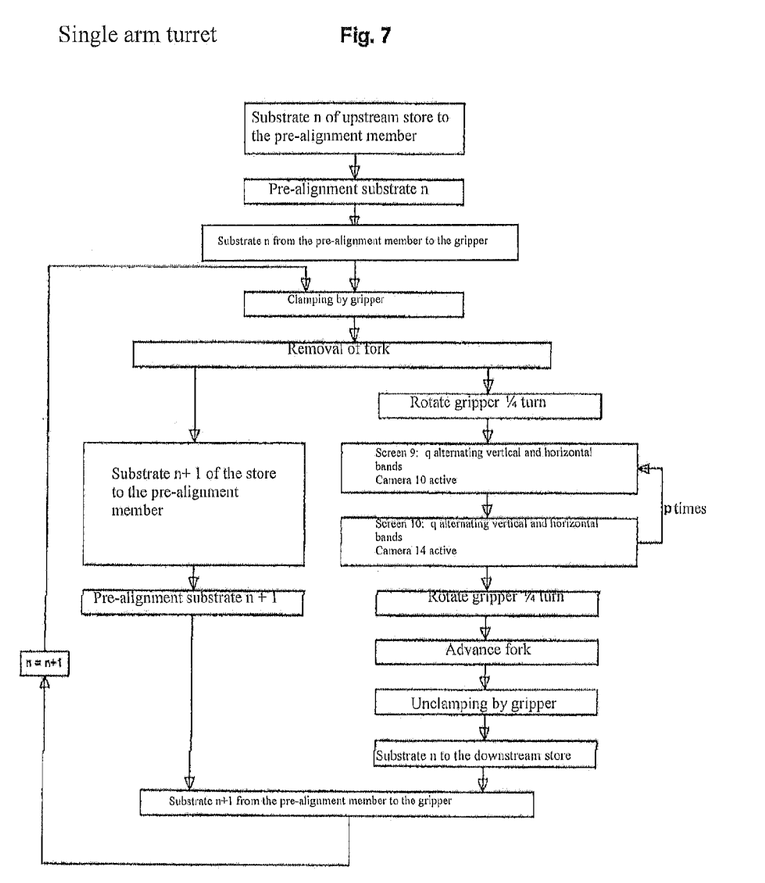
FIGS. 7 and 8 are flow charts of steps of the method.

During operation, see FIG. 7, the control unit 26 controls the handling member 21, the gripper 15, the screens 9 and 10 and the cameras 13 and 14. The handling member 21 is presented opposite the container 22 which contains a plurality of substrates to be inspected. The fork 31 passes below a substrate 11 then raises the substrate 11 by a few millimeters and withdraws from the container 22 supporting the substrate 11. The handling member 21 then moves the substrate 11 as far as the prealignment member 24 which brings about appropriate positioning of the substrate 11, for example, using three fingers which are moved with a radial movement and which come into contact with the outer edge 11c of the substrate 11. Then, the fork 31 ensures that the substrate 11 is taken and moves it through the aperture 6 in order to move it between the limbs 18 and 19 of the gripper 15. The fork 31 is located very slightly below the limbs 18 and 19 so that the substrate 11 is located in the region of the limbs 18 and 19. The limbs 18 and 19 are clamped on the outer edge 11c of the substrate 11. The fork 31 is lowered to become disengaged from the substrate 11 which is now held between the limbs 18 and 19, in particular in the grooves 20. The handling member 21 withdraws the fork 31, for example, into the handling chamber 4.

The substrate 11 held between the grippers 18 and 19 in a substantially horizontal starting position, is rotated through a quarter turn in order to move it into the substantially vertical position illustrated in FIG. 1. The control unit 26 then proceeds with the inspection itself by controlling the illumination by the screen 9 of the face 11a of the substrate 11 fixed in position by the gripper 15. The screen 9 displays substantially vertical lines which are alternately luminous and black, then substantially horizontal lines 35 which are alternately luminous (white or colour) and black, for q times, with q being between 1 and 20. Simultaneously, the camera 13 takes images, for example, for a duration of between 100 and 3000 milliseconds. The camera 13 may take a succession of images for each type of line. Then, the screen 9 is switched off and the screen 10 illuminated to illuminate the face 11b of the substrate 11. The screen 10 displays lines which are similar to those of the screen 9, in particular vertical lines 34, see FIG. 2. The camera 14 simultaneously takes one or more images. The images taken by the cameras 13 and 14 are transferred to the control unit 26 which brings about a processing operation in order to verify the presence of faults, in particular faults in the surface flatness or appearance of the faces 11a and 11b of the substrate. This sequential operating mode may advantageously be replaced with a simultaneous mode, where the screen/camera system inspecting the upper face and that inspecting the lower face operate in an independent and simultaneous manner.

In one embodiment, the illumination is provided by the whole surface of the screens 9 and 10. The Applicant has realised that it was advantageous to limit the illumination to an oval zone 32 on the screens 9 and 10 corresponding to the geometric projection of the faces 11a and 11b of the substrate 11 on the screens 9 and 10, respectively. In this instance, the vertical lines 34, then horizontal lines 35 are displayed in the oval zone 32, the outer edge 33 of the screen remaining black. The quantity of light diffused in the inspection chamber 3 is reduced and the interference is reduced for the cameras 13 and 14, which can then provide a signal with improved quality.

Then, since the stationary phase of the substrate 11 in a substantially vertical position has ended, the turret 17 of the gripper 15 controlled by the control unit 26 rotates substantially through a quarter of a turn, to place the substrate 11 in a substantially horizontal position. The fork 31 of the handling member 21 moves below the substrate 11 at a safe distance, for example, in the order of a few millimeters, then moves vertically and climbs at low speed as far as the region of the lower face 11b of the substrate 11. The limbs 18 and 19 then move from the engaged position to the open position, the substrate 11 resting on the fork 31.

The fork 11 leaves the inspection chamber 3 and, moving through the supply chamber 4, places the substrate 11 in the container 22 or 23. The cycle can then be repeated. Of course, in order to increase the productivity of the inspection machine, the handling member 21 can be controlled to take a substrate 11 and convey it to the prealignment member 24 during the steps during which the substrate 11 previously carried to the gripper 15 is being inspected by the cameras 13 and 14.

As can be seen in the flow chart of FIG. 7, the steps of illumination by the screen 9, 10 and observation by the camera 13, 14 may be repeated until sufficiently precise data are obtained. The number of sub-steps p can be between 1 and 10.

Figure 8:
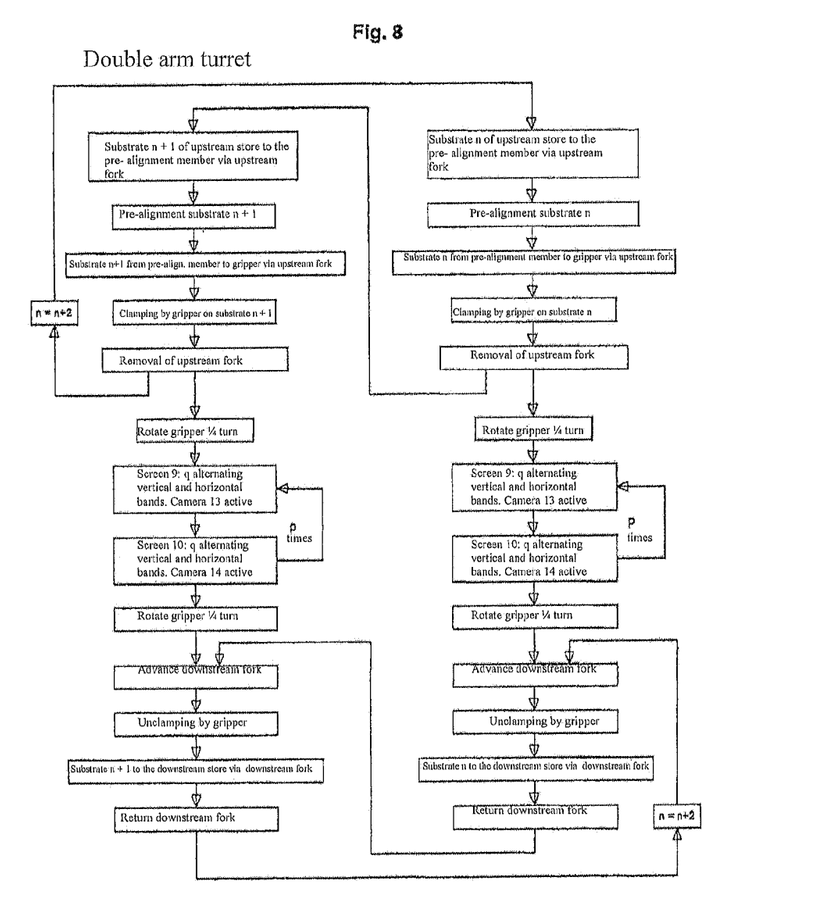
Figure 9:
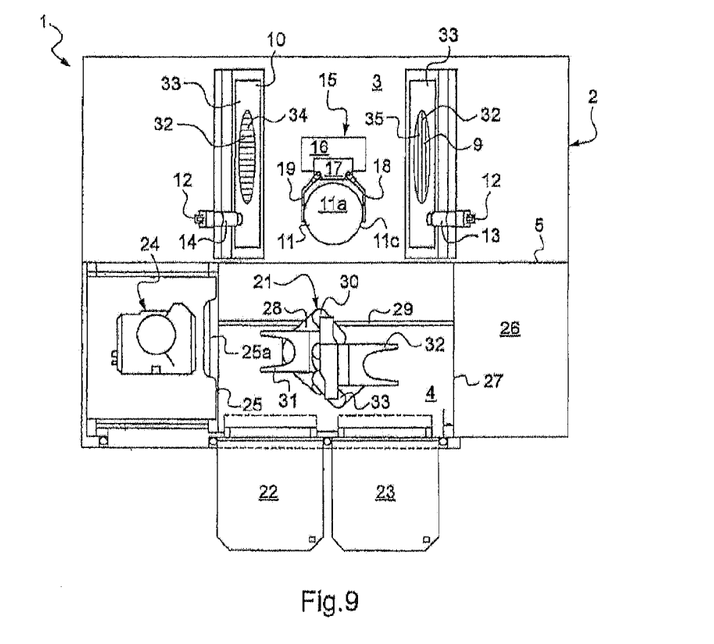
FIG. 9 is a plan view of a flat disc inspection machine.

In the embodiment of FIG. 9, the handling member 21 can be provided with a turret 28 which supports two arms 30, 33, each of which is provided with a fork 31, 32. The productivity of the inspection machine 1 can be improved by following the flow chart of FIG. 8 in so far as the fork referred to as the upstream fork, can be dedicated to the handling steps prior to the inspection by the cameras 13 and 14 whilst the additional fork referred to as the downstream fork can be dedicated to the handling steps following the inspection by the cameras 13 and 14 to move the substrate 11 inspected from the gripper 15 into the container 22 or 23.

Several steps can be carried out simultaneously depending on the respective durations of each step and in particular the duration of the inspection by the cameras 13 and 14. More specifically, the upstream fork may remove a substrate from the prealignment member 24 whilst the preceding substrate is being inspected by the cameras 13 and 14, the upstream fork waiting for the preceding substrate to be removed by the downstream fork. As soon as the downstream fork has removed the preceding substrate 11 from the processing chamber 3, the upstream fork can introduce the following substrate into the processing chamber 3. That is to say, the duration between two inspection steps by the cameras 13 and 14 is reduced, leading to a higher yield.

Furthermore, the upstream fork has two operations to carry out, bringing a substrate 11 to the prealignment member 24, then bringing the substrate 11 to the gripper 15, whilst the downstream fork has one handling operation to carry out: bringing the inspected substrate 11 to the downstream container 23. The control unit 26 can give priority to the upstream fork 31, which again allows the cycle time to be reduced slightly. In this manner, the downstream fork may remain with an inspected substrate awaiting storage whilst the upstream fork carries out another operation, for example, removing a substrate from the container 22 in order to bring it to the prealignment member 24, or removing a substrate 11 from the prealignment member 24.

Furthermore, the control unit 26 can be configured to simultaneously operate the sources of light formed by the screens 9 and 10.

The containers 22 and 23 may be used, one as an upstream container and the other as a downstream container. The containers 22 and 23 may be used, one after the other, a substrate 11 removed from the container 22 returning there after inspection, optionally in the same position.

The invention claimed is:

1. Device for inspecting semiconductor wafers comprising:
    a wafer transport arm which is provided with at least one wafer support element comprising a gripper for gripping wafers, the gripper comprising two remote limbs which are configured to hold opposing edges of the wafer, the gripper being rotatably mounted on a shaft so as to be able to rotate the wafer between a substantially horizontal position and a substantially vertical position, and
    at least two inspection systems which are arranged at one side and the other of the wafer in its substantially vertical position, symmetrically relative to the plane which extends through the wafer,
    wherein each inspection system comprises at least one light source and at least one camera, each camera being positioned in order to capture the light reflected by the surface of the wafer opposite it and each light source being positioned in order to transmit an incident light beam towards the surface,
    wherein each light source comprises a video screen arranged to illuminate a respective face of the wafer, and
    wherein, during use, the inspection systems are actuated when the wafer is immobile in a substantially vertical position.

2. Device according to claim 1, wherein the transport arm comprises at least two articulation axes and is supported by a turret which supports at least one wafer transport arm, the turret being translatably mounted on a sliding member.

3. Device according to claim 1, wherein each limb of the gripper has a groove which is provided on a surface arranged opposite the other limb.

4. Device according to claim 3, wherein the groove is generally V-shaped.

5. Device according to claim 1, wherein at least one of the limbs is mounted for pivoting about an axis which is substantially perpendicular relative to the plane of the wafer held between the limbs.

6. Device according to claim 1, wherein the transport elements have a lateral spatial requirement smaller than the opening between the limbs of the gripper.

7. Device according to claim 1, wherein each light source comprises a monitor whose smallest dimension is more than 1.5 times greater than the maximum opening between the limbs of the gripper.

8. Device according to claim 7, wherein the monitor comprises an LCD or plasma screen.

9. Device according to claim 1, wherein the camera is arranged above the light source.

10. Device according to claim 1, further comprising a control unit which is configured to control the display of parallel lines by the light sources.

11. Device according to claim 10, wherein the control unit comprises at least one output which is connected to a camera and at least one output which is connected to the corresponding light source in order to synchronize the camera and the light source.

12. Device according to claim 10, wherein the control unit is configured to control an illuminated oval zone of the light source and a dark outer edge.

13. Device according to claim 10, wherein the control unit is configured to control the display of different colors simultaneously by the light sources.

14. Device according to claim 10, wherein the control unit is configured to control an alternating illumination by the light sources.

15. Method for inspecting semiconductor wafers, comprising:
conveying a semiconductor wafer to be inspected by at least one support element belonging to a transport arm, the support element comprising remote limbs, which are part of a gripper, wherein the gripper grips opposite edges of the wafer;
rotating the gripper about a shaft which causes the wafer to move from a substantially horizontal position to a substantially vertical position; and
while the gripper holds the wafer in a fixed substantially vertical position, actuating at least two inspection systems, which are arranged at one side and the other of the wafer in its substantially vertical position, symmetrically relative to the plane which extends through the wafer,
wherein each inspection system comprises at least one light source and at least one camera, each camera being positioned in order to capture the light reflected by the surface of the wafer opposite it and each light source being positioned in order to transmit an incident light beam towards the surface;
wherein each light source comprises a video screen arranged to illuminate a respective face of the wafer.

16. The method according to claim 15, wherein each light source of each of the inspection systems illuminates the wafer with a wavelength light that is different from the wavelength of light used by the other inspection system.

17. The method according to claim 15, wherein each light source is alternatively activated such that only one light source is illuminating the wafer during inspection.

* * * * *